United States Patent
Hwang et al.

(10) Patent No.: US 9,903,927 B2
(45) Date of Patent: Feb. 27, 2018

(54) APPARATUS AND METHOD FOR CANCELING MAGNETIC FIELDS

(71) Applicant: KOREA RESEARCH INSTITUTE OF STANDARDS AND SCIENCE, Daejeon (KR)

(72) Inventors: Seong-min Hwang, Daejeon (KR); Kiwoong Kim, Daejeon (KR); Jin Mok Kim, Daejeon (KR); Yong-Ho Lee, Daejeon (KR); Chan Seok Kang, Daejeon (KR); Kwon Kyu Yu, Daejeon (KR); Seong-Joo Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 1304 days.

(21) Appl. No.: 13/909,564

(22) Filed: Jun. 4, 2013

(65) Prior Publication Data
US 2013/0271145 A1    Oct. 17, 2013

Related U.S. Application Data

(63) Continuation of application No. PCT/KR2011/007560, filed on Oct. 12, 2011.

(30) Foreign Application Priority Data

Dec. 27, 2010  (KR) .................. 10-2010-0135763

(51) Int. Cl.
*G01V 3/00* (2006.01)
*G01R 33/421* (2006.01)
(Continued)

(52) U.S. Cl.
CPC .......... *G01R 33/421* (2013.01); *A61B 5/0046* (2013.01); *A61B 5/055* (2013.01); *G01R 33/445* (2013.01)

(58) Field of Classification Search
CPC .................................................. G01R 33/421
(Continued)

(56) References Cited

U.S. PATENT DOCUMENTS

| 4,646,046 A * | 2/1987 | Vavrek | G12B 17/02 |
| | | | 174/384 |
| 4,651,099 A * | 3/1987 | Vinegar | G01R 33/28 |
| | | | 174/384 |

(Continued)

FOREIGN PATENT DOCUMENTS

| KR | 10-2009-0128735 | 12/2009 |
| WO | WO 2012/091260 | 7/2012 |

OTHER PUBLICATIONS

International Search Report for PCT/KR2011/007560 dated May 17, 2012.
(Continued)

*Primary Examiner* — Louis Arana
(74) *Attorney, Agent, or Firm* — Jenkins, Wilson, Taylor & Hunt, P.A.

(57) ABSTRACT

Provided are an apparatus and a method for canceling magnetic fields. The apparatus includes a magnetic field canceling coil disposed adjacent to an inner wall of a magnetic shield room to surround the entire inner space or a portion of an inner space of the magnetic shield room; and a magnetic field canceling coil driver to supply current to the magnetic field canceling coil. The magnetic field canceling coil cancels a prepolarization magnetic field established on the wall of the magnetic shield room by a prepolarization coil disposed in the center of the magnetic shield room to minimize magnetic interference caused by the magnetic shield room.

13 Claims, 16 Drawing Sheets

(51) Int. Cl.
*A61B 5/00* (2006.01)
*A61B 5/055* (2006.01)
*G01R 33/44* (2006.01)

(58) Field of Classification Search
USPC .................................................. 324/318, 322
See application file for complete search history.

(56) References Cited

U.S. PATENT DOCUMENTS

| | | | |
|---|---|---|---|
| 5,136,273 A * | 8/1992 | Ohta | G01R 33/421 |
| | | | 324/319 |
| 5,488,339 A | 1/1996 | Havens et al. | |
| 6,504,461 B2 | 1/2003 | Huang et al. | |
| 7,525,314 B1 * | 4/2009 | Heiland | G01R 33/025 |
| | | | 324/318 |
| 2006/0055406 A1 | 3/2006 | Lvovsky et al. | |
| 2014/0084925 A1 * | 3/2014 | Nieminen | G01R 33/421 |
| | | | 324/309 |

OTHER PUBLICATIONS

Written Opinion for Application No. PCT/KR2011/007560 dated May 17, 2012.

\* cited by examiner

APPARATUS AND METHOD FOR CANCELING MAGNETIC FIELDS

CROSS-REFERENCE TO RELATED APPLICATIONS

This application is a continuation of and claims priority to PCT/KR2011/007560 filed on Oct. 12, 2011, which claims priority to Korea Patent Application No. 10-2010-0135763 filed on Dec. 27, 2010, the entireties of which are both hereby incorporated by reference.

BACKGROUND OF THE INVENTION

1. Field of the Invention

The present invention relates apparatuses for cancelling magnetic fields and, more particularly, to magnetic field shielding of a magnetic resonance imaging apparatus.

2. Description of the Related Art

Magnetic resonance imaging (MRI) is a non-invasive technique of imaging the inner part of an imaging object by detecting electromagnetic waves generated during the precession using the nuclear magnetic resonance (NMR) that is a phenomenon involved with precession of the magnetic spin of an atomic nucleus arising from resonance of the magnetic spin of the nucleus under a strong magnetic field when the magnetic field is applied to the atomic nucleus. The MRI is widely used as a medical diagnostics tool to image the inner part of human body.

Ultra-low field NMR and MRI are promising methods in which a magnetic field established by a main magnet that is a core part of conventional NMR and MRI (hereafter collectively referred to as "MRI") is divided into two roles such as the detection magnetic field from several microTesla (µT) to tens of µT. The main magnet for conventional MRI is required to uniformly form a high magnetic field of 0.1 Tesla (T) to several Tesla. Therefore, the main magnet is large in volume and high in cost.

A main magnet coil for a conventional MRI apparatus is divided into two parts such as a polarization coil and a pickup coil in an ultra-low field MRI apparatus. A prepolarization magnetic field established by the polarization coil polarizes an object to be imaged (hereinafter referred to as "imaging target"). The pickup coil applies a detection magnetic field to the imaging target. Then, a nuclear magnetic resonance signal generated during relaxation of a magnetic spin of a nuclear of the polarized imaging target is detected while the prepolarization magnetic field is turned off. In such an ultra-low field MRI apparatus, a prepolarization coil has only to establish a strong prepolarization magnetic field although uniformity of the prepolarization coil is reduced. Thus, a nuclear magnetic resonance apparatus has a simple structure and the manufacturing cost of the nuclear magnetic resonance apparatus is significantly reduced.

In addition, since the detection magnetic field does not serve to polarize the imaging target, the intensity of the nuclear magnetic resonance signal may be maintained although the strength of the detection magnetic field is low. In the case of high field MRI, a frequency of a pickup signal corresponding to the Larmor frequency that is in proportion to the magnitude of a magnetic field is several tens of MHz. In the case of a detection magnetic field of tens of µT in ultra-low field MRI, a frequency of a pickup signal is several kHz. In the case of a detection magnetic field of several µT in ultra-low field MRI, a frequency of a pickup signal is hundreds of Hz. For this reason, a phenomenon which cannot be observed using conventional high field MRI may be observed.

Since the magnitude of a magnetic field applied during measurement is low, distortion caused by a metal within or around an imaging target is significantly reduced. Thus, the ultra-low field MRI may be applied without difficulty to a person who wears a metal prosthesis. In addition, the ultra-low field MRI may non-invasively obtain an inner image of a metal can. Furthermore, the ultra-low magnetic field MRI may be applied to the security field besides the medical diagnosis that is a field of conventional MRI. For example, the ultra-low magnetic field may complement or replace conventional X-ray that is used to obtain security images.

Unlike a main magnetic field of high field MRI, a prepolarization magnetic field need not be highly uniform. Accordingly, a prepolarization coil is not limited to a complex shape where a shimming coil is added to a hollow cylinder surrounding an object to be measured (hereinafter referred to as "measurement target") and may have various shapes such as a thick cake-like shape. Since the magnitude of a magnetic field established by a detection magnetic field coil is low, the detection magnetic field coil is spatially enough to be established. There may be provided an open-type design where a measurement target is disposed below a prepolarization coil.

An ultra-low field MRI apparatus requires a gradient magnetic field to add signal generation position information to a magnetic resonance signal, besides the detection magnetic field for NMR. The detection magnetic field and the gradient magnetic field must be very uniform spatially and constant over time. Thus, the earth's magnetic field and an external magnetic field must be prevented from having an influence on the ultra-low field MRI. In addition, a weak magnetic resonance signal generated by the ultra-low field MRI must be prevented from being contaminated by various external magnetic and electromagnetic noises.

There are two methods for overcoming the above problems. One of the methods is an active shielding method. For example, a triaxial magnetic field sensor and a triaxial Helmholtz coil are mounted around an ultra-low field MRI apparatus. The magnetic field sensor measures an external magnetic field. The Helmholtz coil is supplied with current to cancel the measured magnetic field.

The other method is a passive shielding method. For example, a magnetic shield room is provided around an ultra-low field MRI apparatus. The magnetic shield room is basically made of a plurality of sheet materials having very high magnetic permeability such as mu-metal for blocking external static magnetic fields such as the earth's magnetic field and a low-frequency magnetic field and a metal sheet material having high electric conductivity such as aluminum for blocking a high-frequency magnetic field and an electromagnetic wave.

The active shielding method is advantageous in simple implementation, but its shielding efficiency and property are not good. Moreover, a frequency band of a shielded magnetic field is limited to extremely some parts of a static magnetic field and a low frequency. On the other hand, the passive shielding method using a magnetic shield room is advantageous in excellent shielding efficiency and wide frequency band of a magnetic field. However, the magnetic shield room incurs high cost and occupies a wide space. Due to the advantage and the disadvantage, a low-cost MRI apparatus employs an active shielding method.

However, a strong and intermittent prepolarization magnetic field that is essential to an ultra-low field MRI apparatus polarizes or excites a wall of a magnetic shield room to generate strong eddy current. The polarization of the wall of the magnetic shield room and the eddy current generated on the wall interfere with magnetic resonance of a measurement target to make it difficult for the ultra-low field MRI apparatus to obtain an effective magnetic resonance signal.

SUMMARY OF THE INVENTION

Embodiments of the present invention provide a method for canceling magnetic fields which is capable of effectively preventing a strong prepolarization magnetic field from having an influence on a magnetic shield room.

Embodiments of the present invention also provide an apparatus for canceling magnetic fields which is capable of effectively preventing a strong prepolarization magnetic field from having an influence on a magnetic shield room.

An apparatus for canceling magnetic fields according to an embodiment of the present invention may include a magnetic field canceling coil disposed adjacent to an inner wall of a magnetic shield room to surround the entire inner space or a portion of an inner space of the magnetic shield room; and a magnetic field canceling coil driver to supply current to the magnetic field canceling coil. The magnetic field canceling coil cancels a prepolarization magnetic field established on the wall of the magnetic shield room by a prepolarization coil disposed in the center of the magnetic shield room to minimize magnetic interference caused by the magnetic shield room.

A method for canceling magnetic fields according to an embodiment of the present invention may include setting a magnetic shield canceling space including a wall of a magnetic shield room; calculating a magnetic field established in the magnetic field canceling space by a prepolarization coil; setting a canceling current space inside the magnetic shield room; calculating magnetic fields established in all places of the magnetic field canceling space per unit current density in all places in the canceling current space to prepare a magnetic field establishment operator matrix; back-calculating current density distribution under a relationship of B=MJ (B being a matrix indicating the magnetic field canceling space, J being a current density distribution indicating the canceling current space, and M being the magnetic field establishment operator matrix); and optimizing an arrangement relationship of a magnetic field canceling coil corresponding to the back-calculated current density distribution.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present invention.

DETAILED DESCRIPTION OF EMBODIMENTS

Figure 1:
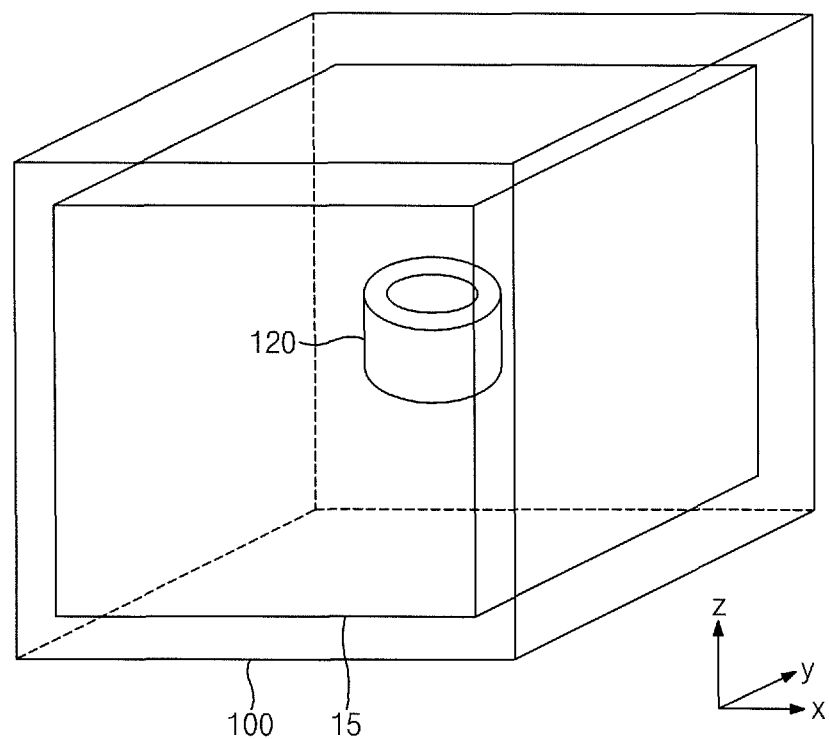
FIGS. 1 and 2 show a space where a prepolarization coil and a magnetic field canceling coil disposed on a wall of a magnetic shield room and within the magnetic shield room are to be located.

An ultra-low magnetic field MRI apparatus is installed in a magnetic shield room to establish a precise magnetic field required for the operation of the apparatus by shielding an external electromagnetic noise and prevent an external magnetic field or an external electromagnetic wave from dispersing a minute magnetic resonance signal or from interfering with the magnetic resonance signal. However, a strong and intermittent prepolarization magnetic field required for an ultra-low field MRI apparatus polarizes or excites a wall of a magnetic shield room, in which the ultra-low magnetic field MRI device is disposed, to generate strong eddy current.

The polarization of the magnetic shield room and the eddy current generated on the wall interfere with magnetic resonance to make it difficult for the ultra-low field MRI device to obtain an effective magnetic resonance signal. In order to overcome the above problem, a prepolarization magnetic field must apply to only a measurement target while having no influence on the magnetic shield room.

For achieving this, a magnetic field canceling coil is disposed close to an inner wall of a magnetic shield room. A magnetic field generated by the magnetic field canceling coil may most effectively cancel a prepolarization magnetic field on the wall of the magnetic shield room while having a slight influence on the prepolarization magnetic field applied to a measurement target. Accordingly, the detailed configuration of the magnetic field canceling coil and the arrangement of individual conductors may be optimized by solving an inverse problem between current density and a magnetic field.

In the manufacturing of an ultra-low field MRI apparatus, there are two factors to limit the magnitude of a prepolarization magnetic field. One of the factors is driving capability of a driving unit which supplies current to a coil for establishing a prepolarization magnetic field. The other factor is to have no influence on a magnetic shield room.

A magnetic shield room has high magnetic field shield efficiency. However, there are many considerations in use of the magnetic shield room to keep shield performance of the magnetic shield room. For example, a magnetic object is inhibited from entering the magnetic shield room. This is because a strong magnetic field established by the magnetic object magnetizes a metal sheet material with high magnetic permeability among parts constituting the magnetic shield room. As a result, the shield performance of the magnetic shield room may be degraded.

A similar problem may occur when an ultra-low field MRI apparatus is disposed within the magnetic shield room. When the ultra-low field MRI apparatus operates, a strong prepolarization magnetic field of about 0.1 Tesla (T) is established and disappears for a short time of about 10 millseconds (ms). The strong prepolarization magnetic field is stronger than a magnetic field established by a strong magnetic object and may polarize the magnetic shield room. In addition, when the strong prepolarization magnetic field is established and disappears at high speed, strong eddy current is generated at a metal sheet (e.g., aluminum) with high electric conductivity for shielding a radio-frequency (RF) magnetic field. The eddy current establishes a residual magnetic field in the magnetic shield room while revolving around the magnetic shield room. The eddy current is attenuated by electrical resistance of the metal sheet material itself after variation of the prepolarization magnetic field is stopped. However, since the electrical resistance of the metal sheet material is extremely low, relaxation time required until the eddy current disappears completely may be several seconds.

A time to measure a magnetic resonance signal for an ultra-low field MRI apparatus is one to two seconds when a nuclear magnetic spin of a measurement target polarized by a prepolarization shield is relaxed. Within the relaxation time of the nuclear magnetic spin, the residual magnetic field established by the eddy current of the magnetic shield room may disperse a uniform detection magnetic field and a gradient magnetic field of the ultra-low field MRI apparatus. Thus, the quality of a magnetic resonance signal may be degraded. In the worse case, the magnetic resonance signal may not be detected.

For example, the magnetic shield room is a cube with six sides of 2 meters (m). A prepolarization coil is disposed in the magnetic shield room. The diameter of the prepolarization coil is 35 millimeters (mm), and the length thereof is 60 mm. The prepolarization coil establishes a prepolarization magnetic field of about 50 milliTesla (mT). In this case, a clear magnetic resonance signal was detected.

On the other hand, the prepolarization coil is disposed in the above magnetic shield room. The diameter of the prepolarization coil is 230 mm, and the length thereof is 130 mm. The prepolarization coil established a prepolarization magnetic field of 15 mT. In this case, a magnetic resonance signal was measured well. As the prepolarization magnetic field increases above 15 mT, the magnetic resonance signal was further degraded. As a result, the magnetic resonance signal disappeared when the prepolarization magnetic field reached 50 mT.

A magnetic field was measured at inner center and inner wall of the magnetic shield room to confirm the fact that such a phenomenon is a problem of a prepolarization magnetic field and a magnetic shield room. Immediately after a prepolarization magnetic field of 100 mT was turned off, a residual magnetic field of about tens of nanoTesla (nT) was established in an opposite direction of the prepolarization magnetic field. It took two or more seconds until the residual magnetic field disappeared. In addition, it was measured that the magnitude of the residual magnetic field was greater on the wall of the magnetic shield room than at the center of the magnetic shield room. As a result, it was confirmed that the source of the residual magnetic field was based on polarization of the wall of the magnetic shield room caused by variation of a prepolarization magnetic field and eddy current induced to the wall.

Both a measurement magnetic field and a gradient magnetic field of the ultra-low field MRI apparatus have about several microTesla (µT). Eddy current generated by the magnetic shield room establishes a residual magnetic field of tens of nanoTesla (nT). Accordingly, normal acquisition of a magnetic resonance signal may be sufficiently impeded to the level of one percent of the measurement magnetic field and the gradient magnetic field.

Thus, there is a need for a method for canceling a residual magnetic field established by polarization of the wall of the magnetic shield room and eddy current induced to the wall.

An apparatus for canceling magnetic fields according to an embodiment of the present invention includes a magnetic field canceling coil disposed to surround an inner space just inside a wall of a magnetic shield room. A magnetic field established by the magnetic field canceling coil most efficiently cancels a prepolarization magnetic field established around the wall of the magnetic shield room. For achieving this, a current density distribution of a magnetic field canceling coil capable of canceling the prepolarization magnetic field is back-calculated. Then, a structure of a magnetic field canceling coil forming a current density distribution closest to the back-calculated current density distribution is found. Then, positive current having the same amount as current flowing to the prepolarization coil or being proportional to the current flowing to the polarization coil at a constant rate is made to reversely flow to the magnetic field canceling coil. Thus, a prepolarization magnetic field established on the wall of the magnetic shield room is canceled.

The present invention will now be described more fully hereinafter with reference to the accompanying drawings, in which preferred embodiments of the present invention are shown. However, the present invention may be embodied in many different forms and should not be construed as limited to the embodiments set forth herein. Rather, these embodiments are provided so that this disclosure will be thorough and complete, and will fully convey the scope of the present invention to those skilled in the art. Like numbers refer to like elements throughout.

Figure 2:
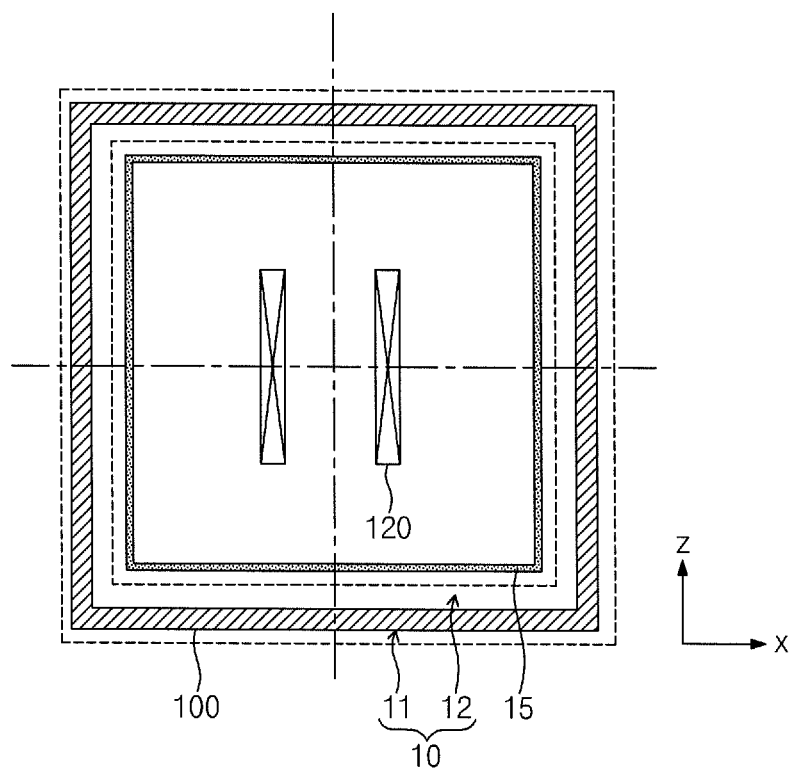

FIGS. 1 and 2 show a space where a prepolarization coil and a magnetic field canceling coil disposed on a wall of a magnetic shield room and within the magnetic shield room are to be located.

Referring to FIGS. 1 and 2, an ultra-low field MRI apparatus including a prepolarization coil 120 is disposed within a magnetic shield room 100. A magnetic field canceling coil (not shown) is disposed adjacent to a wall of the magnetic shield room 100 along the wall and disposed to surround the inside of the magnetic shield room 100.

Mathematical inverse problem analysis may be employed to obtain a current density distribution of a magnetic field canceling coil capable of most effectively canceling a magnetic field established in a space around the wall of the magnetic shield room 100. That is, the current density distribution of a magnetic field canceling coil is calculated where a canceling magnetic field generated by a magnetic field canceling coil in a space around an inner wall of the magnetic shield room becomes closest to a prepolarization magnetic field, in the opposite direction, established by the prepolarization coil in the same space.

Hereinafter, an exemplary structure of a magnetic shield room will now be described below.

The inner space of the magnetic shield room 100 has height of 2 meters (m) and width of 2 m. An outer wall of the magnetic shield room 100 has thickness of 20 centimeters (cm). In the internal center of the magnetic shield room 100, the prepolarization coil 120 is disposed in the form of solenoid having outer diameter of 230 mm, inner diameter of 182 mm, and length of 130 mm. When current of 20 ampere (A) flows to the prepolarization coil 120, a magnetic field of 0.1 T is established in the center of a bore of the prepolarization coil 120. A bore direction (z-axis direction) of the prepolarization 120 faces the ceiling and the floor of the magnetic shield room 100. Resistance of the prepolarization coil 120 is 0.6 ohms, and inductance thereof is 230 milliHenries (mH).

A perpendicular component of the magnetic field applied to an wall of the magnetic shield room 100 by the prepolarization coil 120 is strongest on the ceiling and the floor of the magnetic shield room 100 and has the strength of about 0.2 mT.

A perpendicular component of the magnetic field applied to an wall on four sidewalls of the magnetic shield room 100 by the prepolarization coil 120 has the strength of about 0.09 mT with opposite direction at an upward quarter position and a downward quarter position from the center of the magnetic shield room 100. A wall of the magnetic shield room 100 is polarized by a magnetic field applied to the wall of the magnetic shield room 100, and eddy current is induced to flow in the same direction as flowing to the prepolarization coil.

A magnetic field canceling coil (not shown) is disposed to be spaced at an interval of 10 cm from the inside of the wall of the magnetic shield room 100 to prevent the polarization of the magnetic shield room and the induction of the eddy current. The magnetic field canceling coil has a shape of square box whose height and width are all 1.8 m and enables current to flow in an opposite direction to the flow direction of the eddy current. The individual conductor matrix of the magnetic field canceling coil is optimized to most effectively cancel a magnetic field applied to the wall of the magnetic shield room 100. That is, there is back-calculated an individual conductor matrix method of a magnetic field canceling coil where the sum of a magnetic field established by the prepolarization coil 120 and a magnetic field established by the magnetic field canceling coil is minimized around the wall of the magnetic shield room 100.

First, a magnetic field canceling space 10 is prepared to cancel a magnetic field around the wall of the magnetic shield room 100. The magnetic field canceling space 10 includes an internal magnetic field space surface 12 and an external magnetic field space surface 11. The internal magnetic field space surface 12 may be a surface of hexahedron whose height and width are all 1.9 m corresponding to the middle between the inner wall of the magnetic shield room 100 and the magnetic field canceling coil. The external magnetic field space surface 11 may be a surface of hexahedron whose height is 2.4 m and width is 2.8 m.

Next, a canceling current space 15 is set. Current to cancel a magnetic field of the magnetic field canceling space 10 flows to the canceling current space. The canceling current space 15 has an inner surface whose height and width are all 1.8 m and an outer surface whose height and width are all 1.81 m. Thickness of the canceling current space 15 is 5 mm that is equal to thickness of a conductor to be used in the magnetic field canceling coil. The current flowing direction in the canceling current space 15 is limited to be opposite to the direction of current flowing to the prepolarization coil 120.

Next, magnetic fields established in all the places of a magnetic field cancelling space per unit current density are calculated in all the places of the canceling current space 15, respectively. A magnetic field establishment operator matrix M is prepared. If a matrix indicating magnetic field distribution of the magnetic field canceling space 10 is B, a current density matrix or current density distribution indicating the canceling current space 15 is J, and the magnetic field establishment operator matrix is M, a relationship is satisfied, as below:

$$B = MJ \qquad \text{Equation (1)}$$

The equation (1) is back-calculated to find the current density distribution J where the sum of absolute values of magnitudes of magnetic fields established in the magnetic field space B is minimized with the given magnetic field establishment operator matrix M. The back-calculation method may include a Tikhonov regularization method, a least-square method, a maximum entropy regularization method, a truncated singular value decomposition (TSVD) method, a damped singular value decomposition (SVD) method, a conjugate gradient method or a least-square QR factorization (LSQR) method.

If current is applied to the magnetic field canceling coil in its opposite direction according to the current density distribution J of the back-calculated ideal magnetic field canceling coil, a magnetic field established around the wall of the magnetic shield room 100 is effectively canceled. A structure of a magnetic field canceling coil closest to the current density distribution may be determined. Currents to flow to electric wires constituting the magnetic field canceling coil may all be made identical or not.

Figure 3:
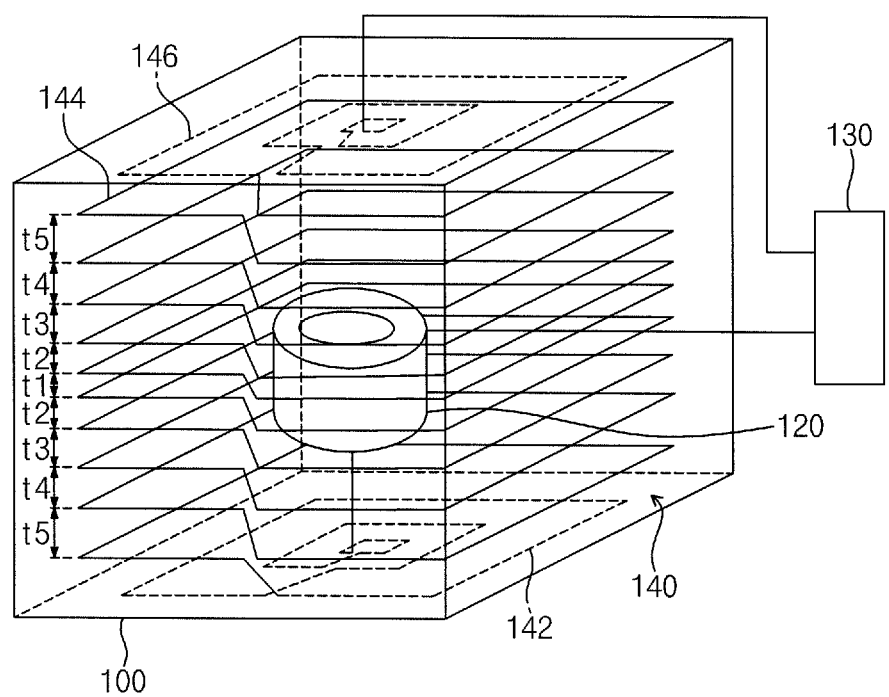
FIGS. 3 and 4 illustrate a magnetic shielding device according to an embodiment of the present invention.
Figure 4:
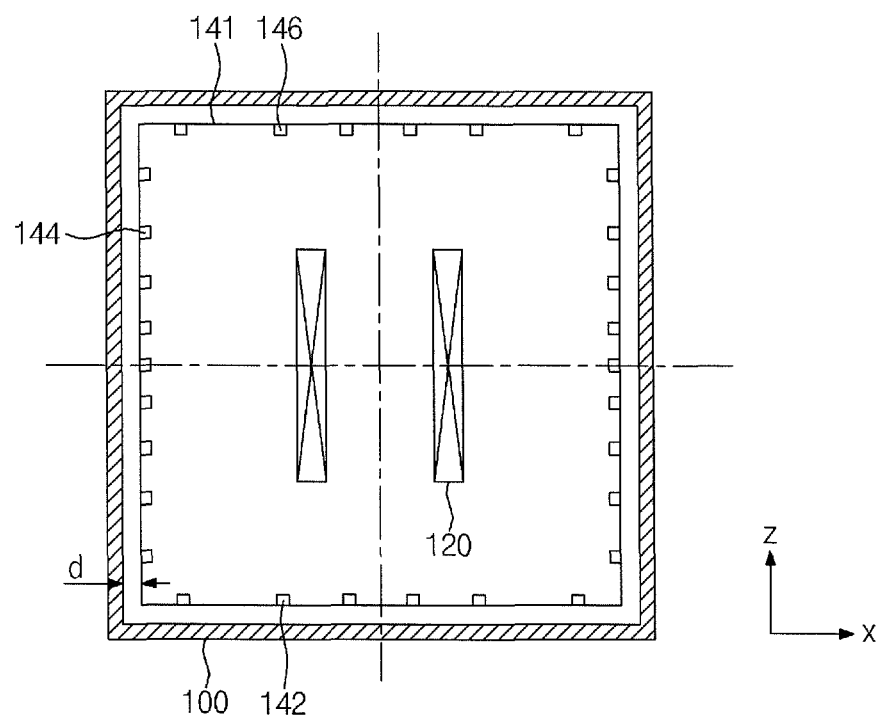

FIGS. 3 and 4 illustrate a magnetic shielding device according to an embodiment of the present invention.

Referring to FIGS. 3 and 4, a magnetic field canceling coil 140 and a prepolarization coil 120 are serially connected to each other. If the same current of 20 A flowing to the prepolarization coil 120 flows to the magnetic field canceling coil 140, an optimal individual conductor matrix of the magnetic field canceling coil 140 corresponding to the obtained current density distribution J may be obtained. In the obtained conductor matrix, the magnitude of the maximum magnetic field applied to the wall of the magnetic shield room 100 was reduced to one-fifth. In addition, a pattern of the magnetic field was transformed into a pattern that makes it difficult to generate eddy current.

The magnetic field canceling coil 140 may include a side coil 144 disposed on an inner side surface of the magnetic shield room 100, a top coil 146 disposed on inner top surface of the magnetic shield room 100, and a bottom coil 142 disposed on an inner bottom surface of the magnetic shield room 100. The side coil 144, the top coil 146, and the bottom coil 142 may be serially connected to each other. The magnetic field canceling coil 140 may be fixed to a support plate 141.

The side coil 144 may include winding wires of the same size that are serially connected to each other. The turn number of winding wires per unit length of the side coil 144 may be maximum at the center position of the side coil 144 and minimum at both ends of the side coil 144. The turn number of winding wires per unit length may be adjusted by intervals t1~t5 of individual conductors.

The top coil 146 or the bottom coil 142 may include winding wires of different sizes that are serially connected to each other on the same plane. The turn number of winding wires per unit length of the top coil 146 or the bottom coil 142 may decrease during increasing depending on a radial direction of the top coil 146 or the bottom coil 142.

More specifically, individual conductors may be arranged such that the amount of current flowing to the magnetic field canceling coil 140 are equal to the current (20 A) flowing to the prepolarization coil 120 and average current density distribution formed by the individual conductors is closest to the current density distribution J. A magnetic field canceling coil including the individual conductors of the determined positions has inductance of within 1 mH and resistance of about 0.1 ohm. The inductance of the magnetic field canceling coil may be much smaller than 230 mH that is the inductance of the prepolarization coil 120. Thus, the magnetic field canceling coil 140 may be serially connected to the prepolarization coil 120 and current driven at a prepolarization coil driver 130 may be used.

When the serially-connected coils (i.e., the magnetic field canceling coil 140 and the prepolarization coil 120) are driven together, the effect of a magnetic field established by the magnetic field canceling coil 140 in the bore center of the prepolarization coil 120 is less than 0.1 percent. In addition, a magnetic field applied to the ceiling and the floor of the magnetic shield room 100 is reduced on average less than 0.015 mT that is only 7.5 percent of a magnetic field of the prepolarization coil 120. A magnetic field 0.04 mT is applied at the outer side of the ceiling and the floor of the magnetic shield room 100. However, the overall distribution of the applied magnetic field is dispersed to make it difficult to generate constant eddy current. Moreover, an area of a polarized wall is significantly reduced.

A magnetic field applied to a side surface of the magnetic shield room 100 disappears at most positions to be less than 0.002 mT that is 5 percent of a magnetic field of the prepolarization coil 120. A magnetic field of maximum 0.02 mT is applied to a position corresponding to one-sixth of the overall height from the side surface to the ceiling and the floor of the magnetic shield room 100. However, an overall area to which the magnetic field is applied is reduced to one-fifth or less than as compared with when there is no magnetic field canceling coil 140. Thus, the overall effect of the magnetic field is reduced to about ¹/₂₅. In addition, in a direction of generated residual eddy current, the direction of eddy currents generated at the side surface is opposite to that of eddy currents generated at the ceiling and the floor of the magnetic shield room 100. Thus, a residual magnetic field generated by eddy current is further reduced.

Figure 5:
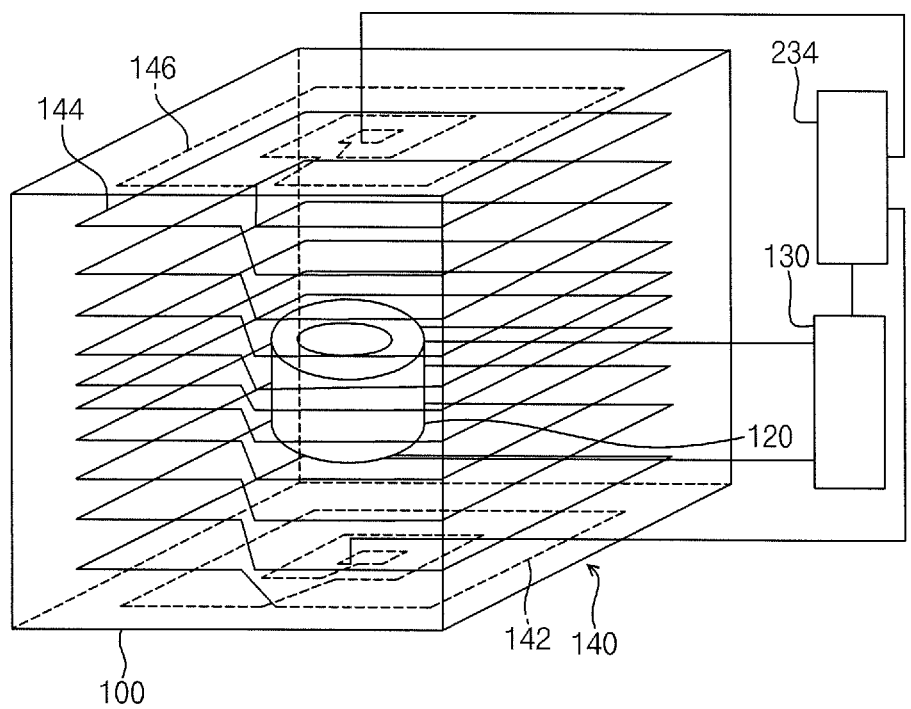
FIGS. 5 and 6 illustrate a magnetic shielding device according to another embodiment of the present invention.
Figure 6:
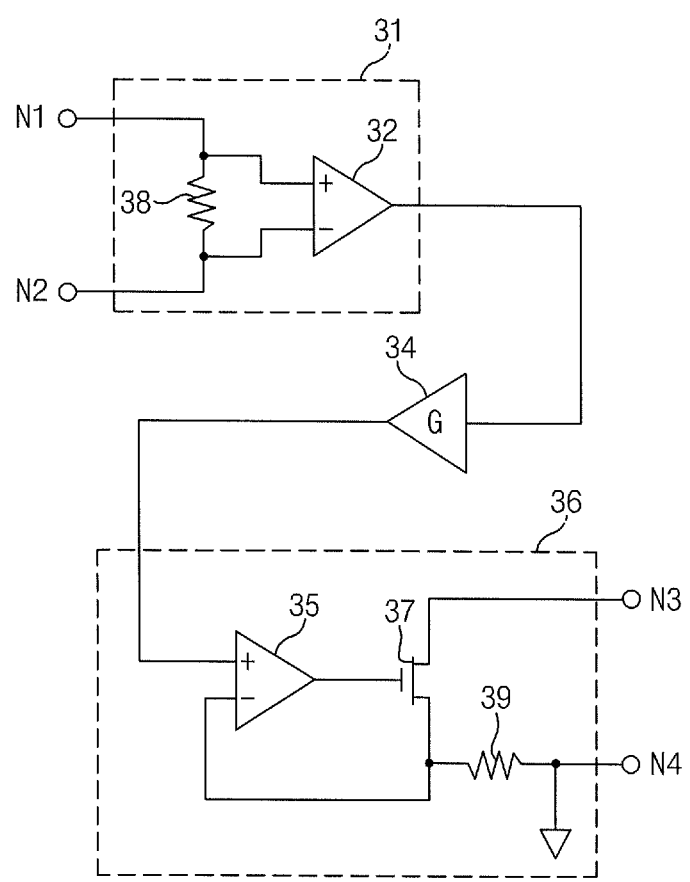

FIGS. 5 and 6 illustrate a magnetic shielding device according to another embodiment of the present invention.

Referring to FIGS. 5 and 6, current flowing to a magnetic field canceling coil 140 may be supplied through a magnetic coil canceling coil driver 234. The magnetic field canceling coil 140 may not be serially connected to a prepolarization coil 120. The current of the magnetic field canceling coil 140 may increase or decrease at a constant rate, unlike current flowing to the prepolarization coil 120. In this case, the magnetic field canceling coil 140 may not be serially connected to the prepolarization coil 140 and may be driven through a separate magnetic field canceling coil driver 234.

The magnetic field canceling coil driver 234 may include a current detector 31 to detect current flowing to the prepolarization coil 120, a signal amplifier 34, and a current driver 36.

The current detector 31 measures current, flowing to the prepolarization coil 120, through a resistor 38 in real time and converts the measured current into an electrical signal. When the prepolarization magnetic field is generated and disappears, a high induced electromotive force of several kV is generated at both ends of the prepolarization coil 120 and introduced in the form of common mode to input terminals N1 and N2 to measure current. The current detector 31 may include a differential amplifier 32 that may withstand a common mode voltage and is high in common mode rejection ration (CMRR).

A gain of the signal amplifier 34 may be more than 1 or less than 1. For a current driver 36 effectively flows current at the magnetic field canceling coil 140 according to an electric signal converted from current measured by the current detector 31, the signal amplifier 34 amplifies or attenuates the converted electrical signal.

The current driver 36 drives the magnetic field canceling coil 140 by converting the amplified or attenuated electrical signal into current. The magnetic field canceling coil 140 may supply current that is in proportion to current flowing to the prepolarization coil 120. Thus, an influence of a strong prepolarization magnetic field on a wall of the magnetic shield room 100 may be minimized.

When current of 4 A that is one-fifth of the current flowing to the prepolarization coil 120 flows to the magnetic field canceling coil 140, the arrangement of the magnetic field canceling coil 140 becomes dense. The magnitude of a magnetic field on the wall of the magnetic shield room 100 is reduced to ¹/₂₀ or less than as compared with when there is no magnetic field canceling coil 140.

Figure 7:
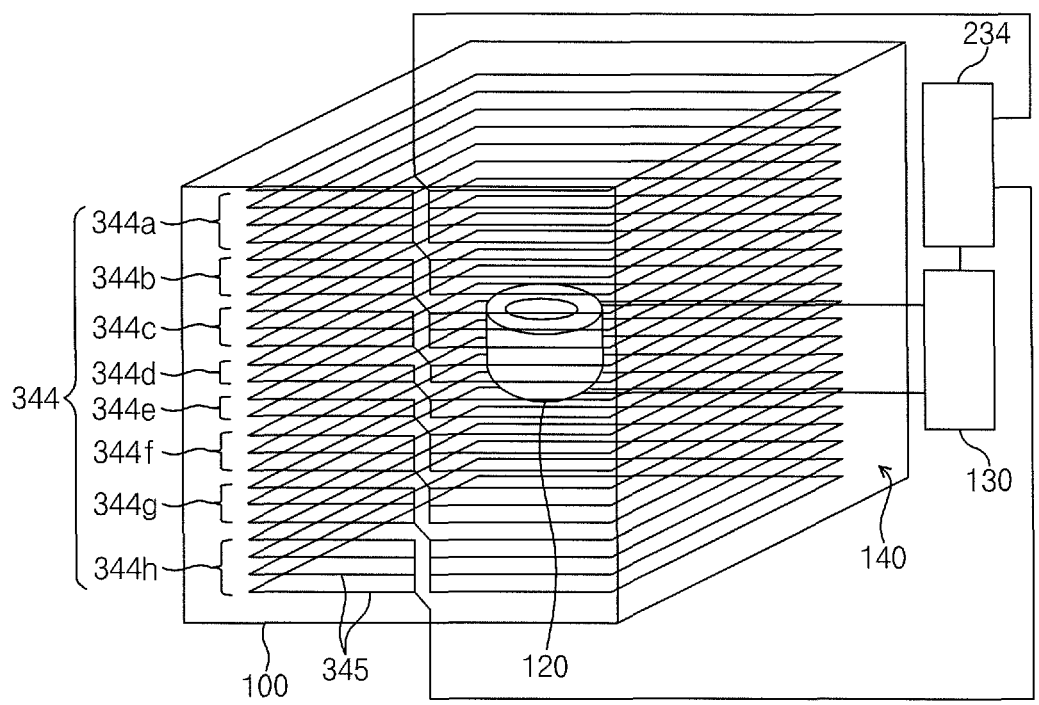
FIG. 7 illustrates a magnetic shielding device according to further another embodiment of the present invention.

FIG. 7 illustrates a magnetic shielding device according to further another embodiment of the present invention.

Referring to FIG. 7, currents to flow to electrical wires constituting a magnetic field canceling coil 140 may all be made different from each other. The turn number of winding coil per unit length of a side coil 344 of the magnetic field canceling coil 140 may be constant. The side coil 344 may be divided into a plurality of unit coils that are serially connected to each other. Individual conductors constituting the unit coil are connected in parallel in at least one of the unit coils to adjust density distribution of current flowing to a coil according to a position of the side coil 344. Current of the magnetic field canceling coil may be supplied by a magnet field canceling coil driver 234.

Individual conductors 345 may be arranged more closely at a place where required current density is low. In this case, adjacent conductors 345 are connected in parallel to each other to match current density distribution with back-calculated optimal current density distribution. A bundle of conductors 344a-344h connected in parallel are connected in series to constitute a magnetic field canceling coil. This method may be used to manufacture a magnetic field canceling coil which is optimized such that practical current density distribution is closer to back-calculated current density distribution.

That is, one or more electrical wires may be connected in parallel and the electrical wires connected in parallel may be connected in series. A method of connecting individual conductors constituting a unit coil in parallel in at least one of the unit coils may adjust current density distribution more closely than a method of connecting all individual conductors in series.

Figure 8:
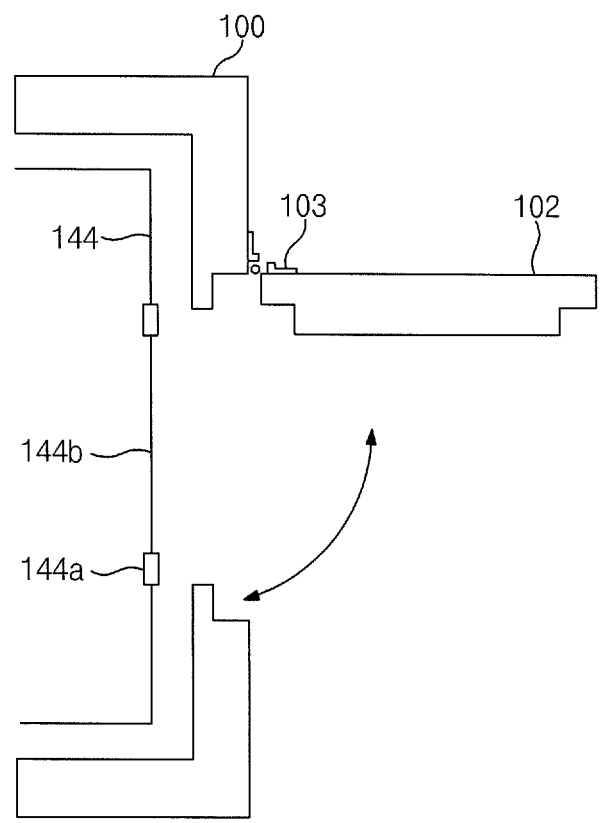
FIGS. 8 and 9 illustrate magnetic shielding devices according to other embodiments of the present invention, respectively.
Figure 9:
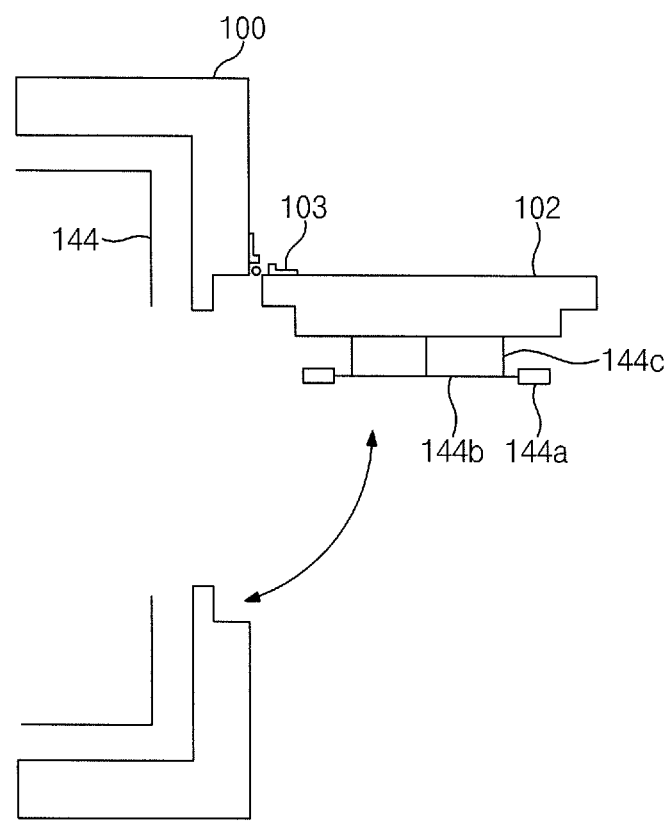

FIGS. 8 and 9 illustrate magnetic shielding devices according to other embodiments of the present invention, respectively.

Referring to FIGS. 8 and 9, a magnetic shield room 100 may include a magnetic shield room door 102. Of a magnetic field canceling coil 144, an individual conductor adjacent to the magnetic shield room door may be removably configured to allow a person or an instrument to enter the inside of the magnetic field canceling coil 144.

When the magnetic field canceling coil 144 is removably configured, a removable portion 144b may be removed independently of the magnetic shield room door 102. The magnetic field canceling coil 144 may be connected to the removable portion 144*b* through an electrical terminal 144*a*.

Alternatively, a removable portion 144*b* of the magnetic field canceling coil 144 may be attached to the magnetic shield room door 102. The magnetic field canceling coil 144 may be connected to the removable portion 144*b* through an electrical terminal 144*a*. When the magnetic shield room door 102 is closed, the removable portion 144*b* and the other fixed magnetic field canceling coil 144 may be directly fastened to each other.

Figure 10:
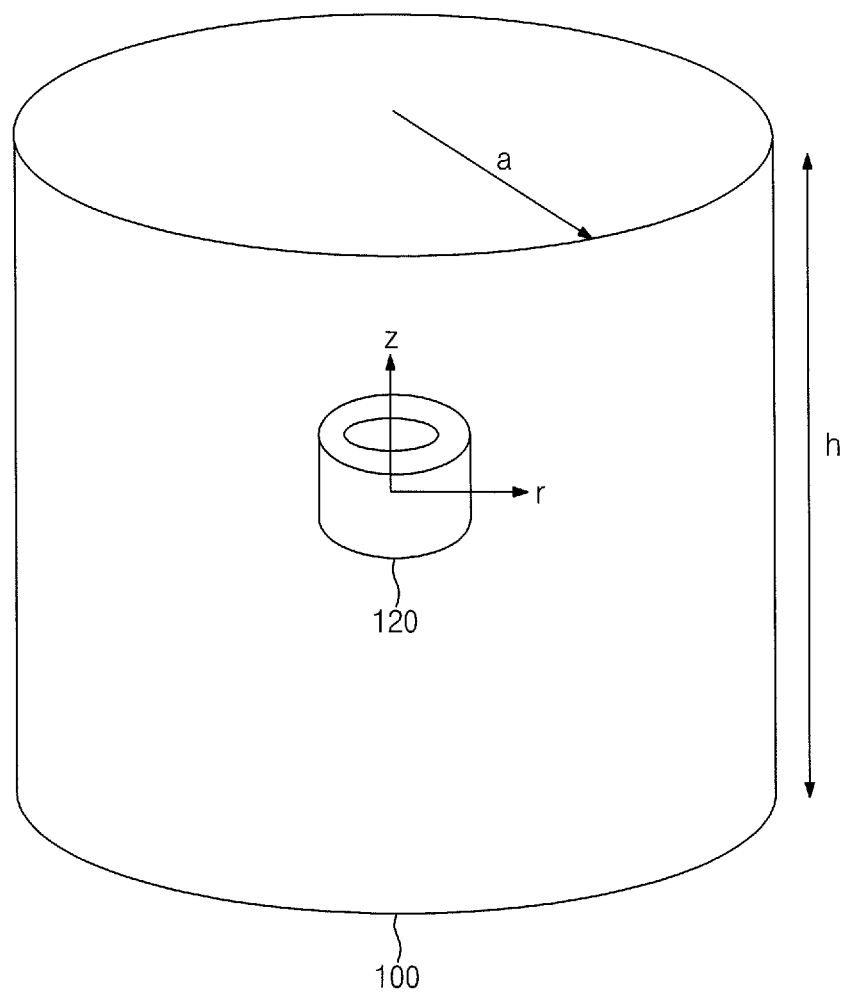
FIG. 10 illustrates an apparatus for canceling magnetic fields according to an embodiment of the present invention.

FIG. 10 illustrates an apparatus for canceling magnetic fields according to an embodiment of the present invention.

Figure 11:
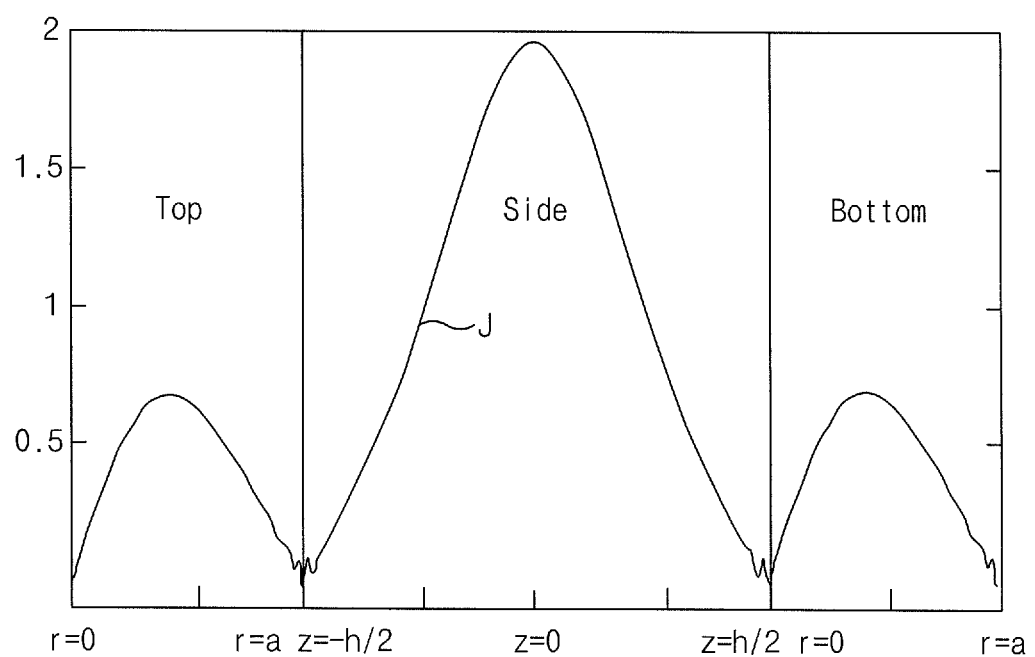
FIG. 11 shows a computer simulation result of current density distribution obtained using a cylindrical coordinate system.

FIG. 11 shows a computer simulation result of current density distribution obtained using a cylindrical coordinate system.

Referring to FIGS. 10 and 11, when a magnetic shield room 100 is cylindrical, its radius is "a" and its height is "h". Current density distribution J on a side surface of the magnetic shield room 100 exhibits the maximum in the center (z=0). In addition, the current density distribution J on top and bottom surfaces of the magnetic shield room 100 exhibits the maximum at a position slightly lower than r=2/a. A magnetic field canceling coil having the current density distribution J is designed.

Figure 12:
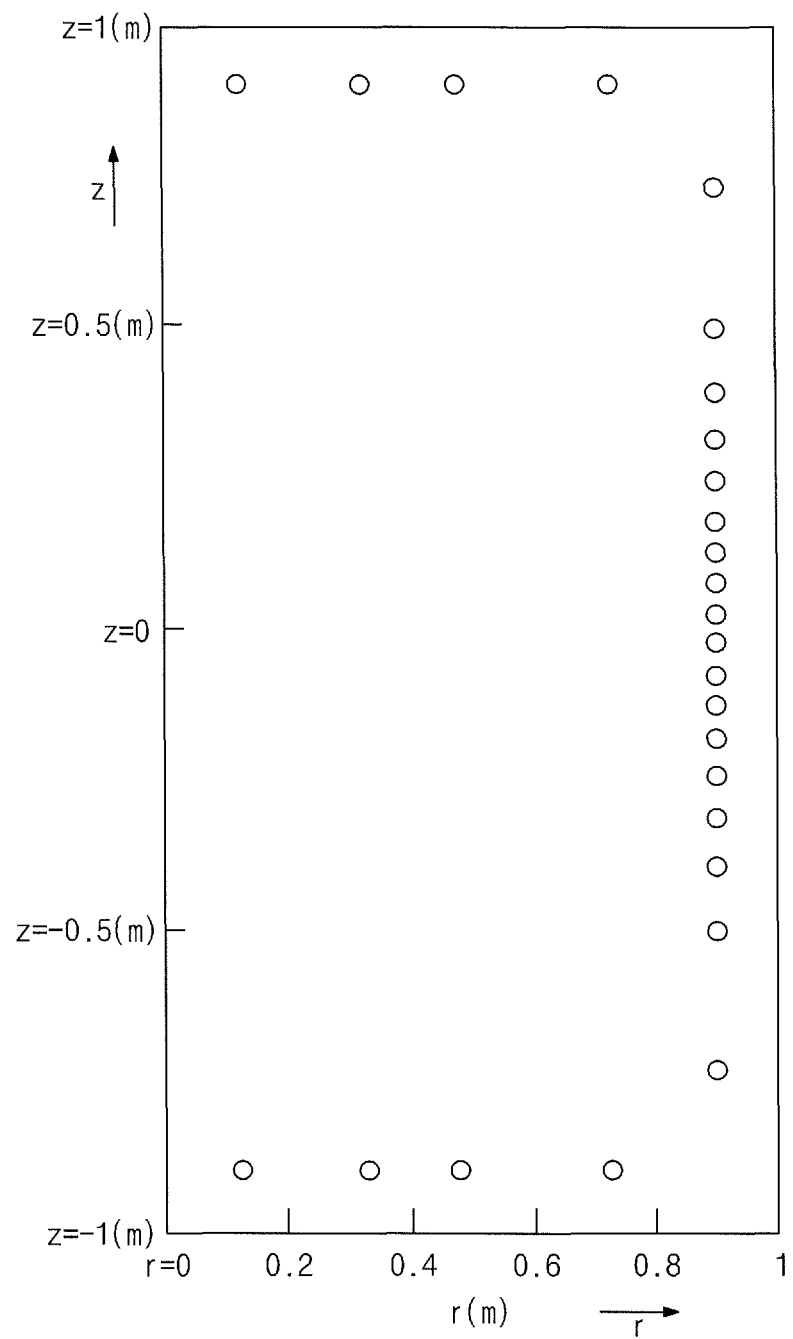
FIG. 12 shows an embodiment for explaining the arrangement of individual conductors of a magnetic field canceling coil set to the current density distribution in FIG. 11.
Figure 13:
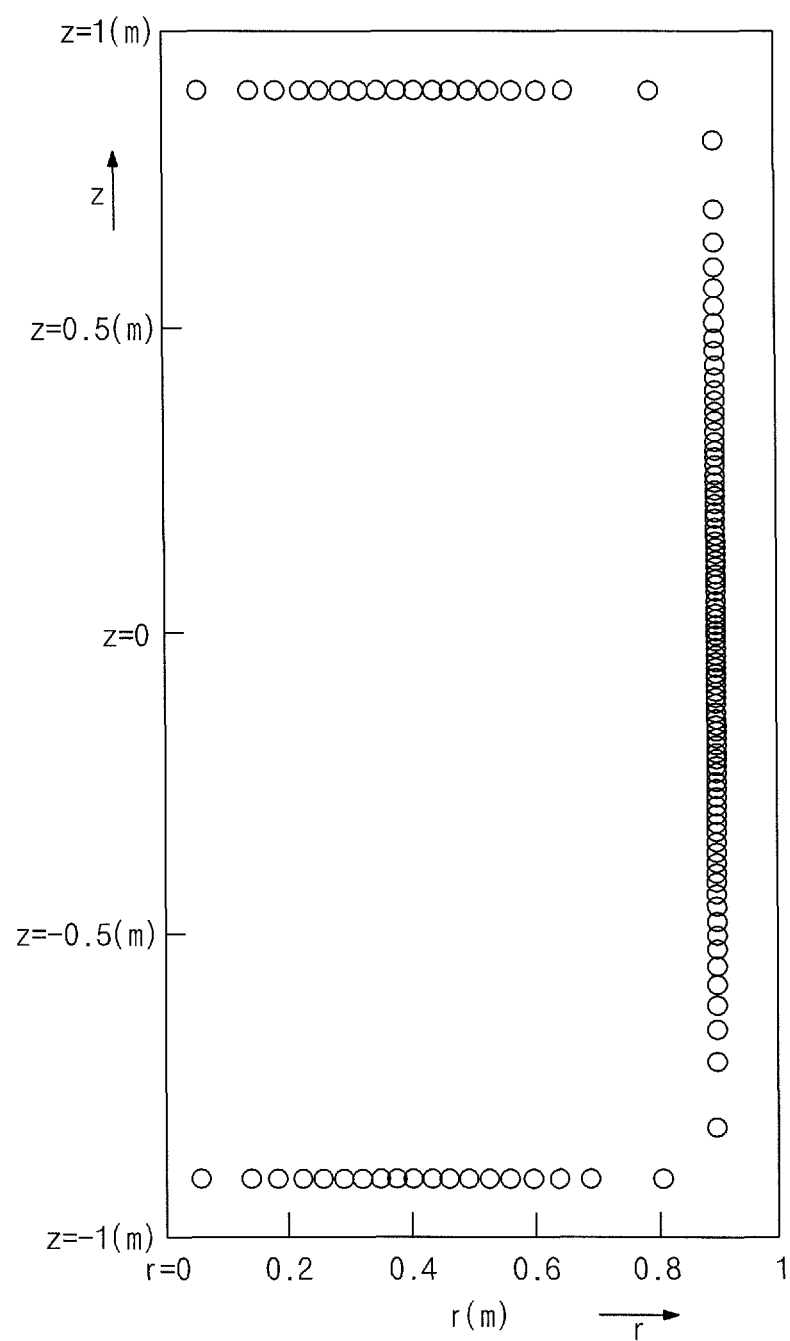
FIG. 13 shows another embodiment for explaining the arrangement of individual conductors of a magnetic field canceling coil set to the current density distribution in FIG. 11.

FIGS. 12 and 13 show individual conductor arrangements optimized through back-calculation of current density of a magnetic field canceling coil according to embodiments of the present invention, respectively.

FIG. 12 illustrates a case where the prepolarization coil and the magnetic field canceling coil are serially connected, as shown in FIG. 3. Currents of the prepolarization coil and the magnetic field canceling coil are all 20 A. An interval of the prepolarization coils is optimized to satisfy the current density distribution described in FIG. 11.

FIG. 13 illustrates a case that the prepolarization coil and the magnetic field canceling coil are independently driven. Current of the prepolarization coil is 20 A, and current of the magnetic field canceling coil is 4 A. An interval of the prepolarization coils is optimized to satisfy the current density distribution described in FIG. 9.

Figure 14:
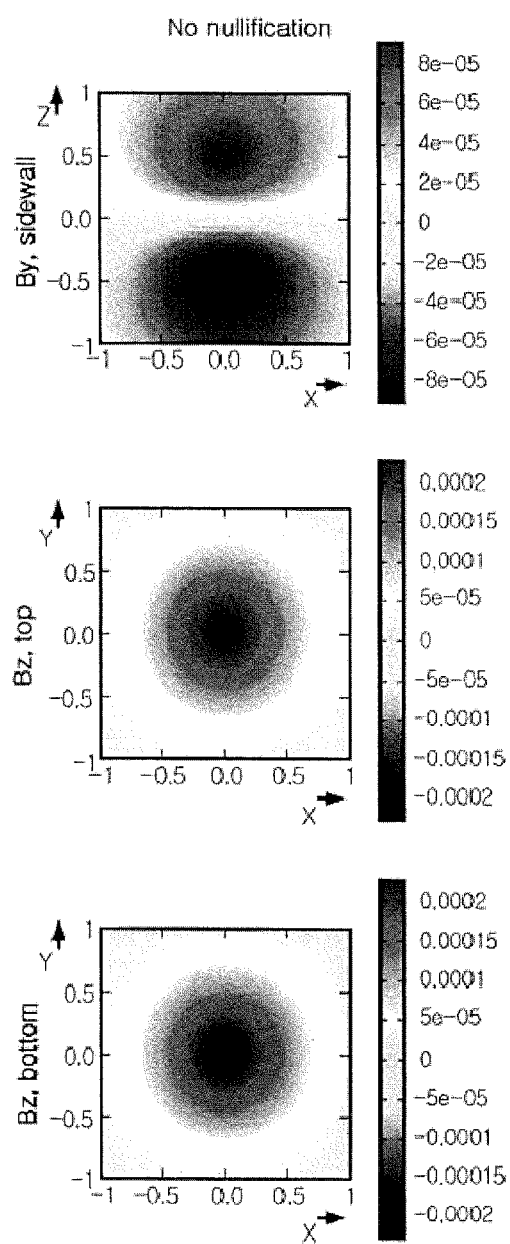
FIGS. 14 to 16 illustrate effects of an apparatus for canceling magnetic fields.
Figure 15:
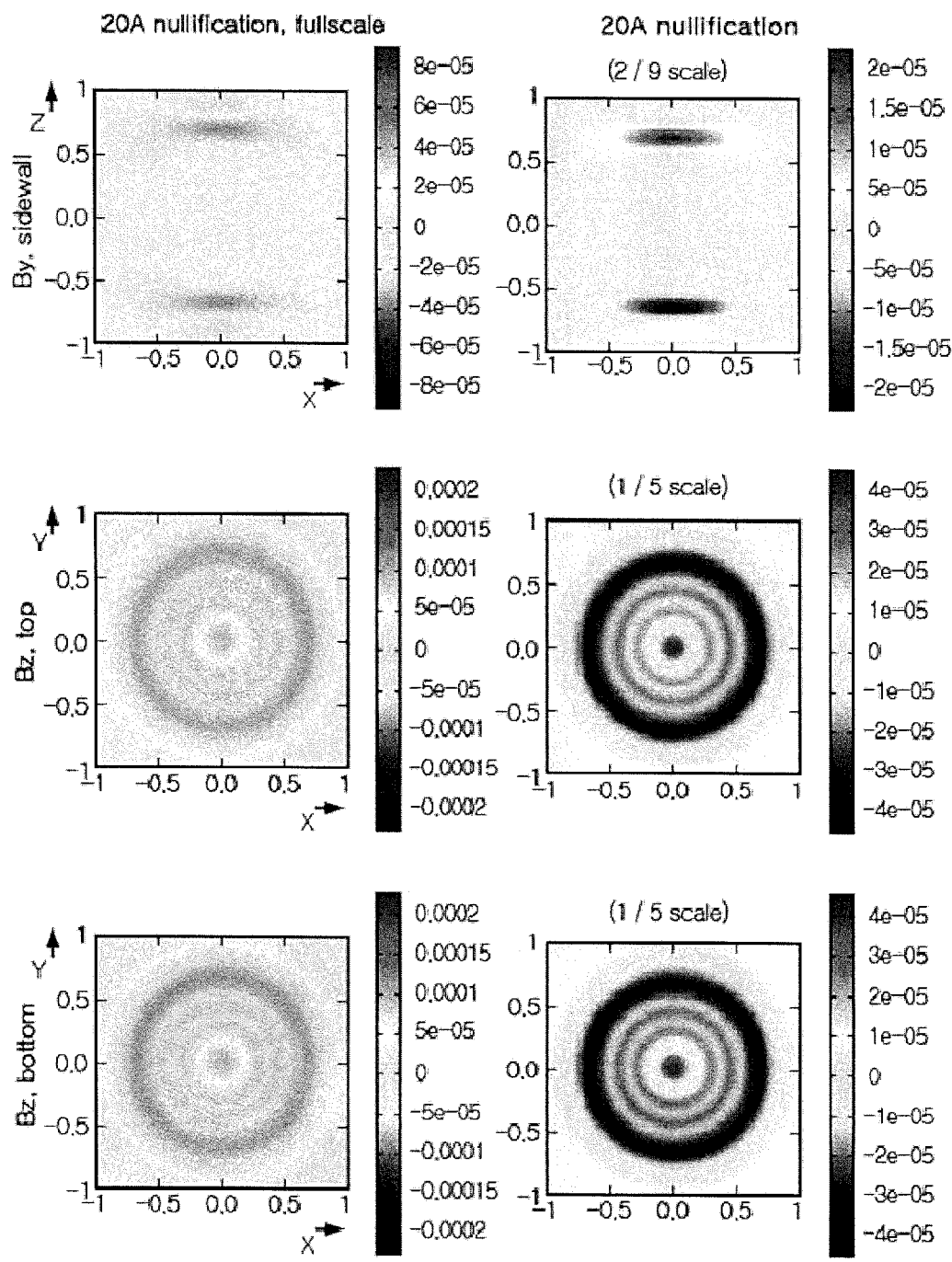
Figure 16:
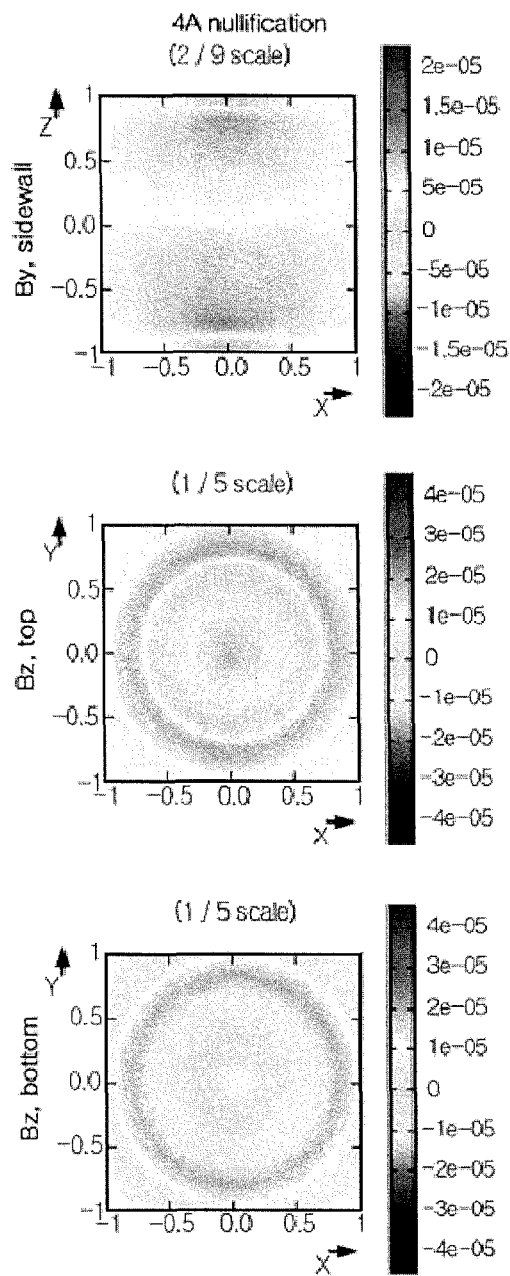

FIGS. 14 to 16 illustrate effects of an apparatus for canceling magnetic fields.

Referring to FIG. 14, in the case that there is no magnetic field canceling coil, a magnetic field established by a prepolarization coil is a magnetic field applied to a wall of a magnetic shield room. From the above, elements perpendicular to the wall of the magnetic shield room are applied to a side surface, a top surface, and a lower surface. In case of the bottom surface and the top surface, the element perpendicular to the wall of the magnetic shield room is a z-axis element. In case of the side surface, the element perpendicular to the wall of the magnetic shield room is a y-axis element facing the outside of the wall. The unit of a colorbar is Tesla (T).

Referring to FIG. 15, in the case that the prepolarization coil and the magnetic field canceling coil are serially connected to each other, a magnetic field established by the prepolarization coil and the magnetic field canceling coil is applied to the wall of the magnetic shield room. As compared to the case that there is no magnetic field canceling coil, the magnet field was reduced to maximum one-fifth. In addition, an area where the magnetic field remains was significantly reduced.

Referring to FIG. 16, in the case that the prepolarization coil and the magnetic field canceling coil are independently driven, a magnetic field established by the prepolarization coil and the magnetic field canceling coil is a magnetic field applied to the wall of the magnetic shield room. As compared to the case that there is no magnetic field canceling coil, the magnetic field was reduced to maximum ¹/₂₀ or less.

As described so far, an apparatus for canceling magnetic fields according to an embodiment of the present invention includes a magnetic field canceling coil to prevent a strong prepolarization magnetic field established by an ultra-low field MRI apparatus from having an influence on a magnetic shield room. The magnetic field canceling coil can prevent the prepolarization magnetic field from polarizing the magnetic shield room and prevent eddy current, which is generated when the prepolarization magnetic field is established and disappears and flows along the wall of the magnetic shield room, from interfering with a magnetic resonance signal.

Although the present invention has been described in connection with the embodiment of the present invention illustrated in the accompanying drawings, it is 200 not limited thereto. It will be apparent to those skilled in the art that various substitutions, modifications and changes may be made without departing from the scope and spirit of the present invention.

What is claimed is:

1. An apparatus for canceling magnetic fields, comprising:
a magnetic field canceling coil disposed adjacent to an inner wall of a magnetic shield room to surround the entire inner space or a portion of an inner space of the magnetic shield room; and
a magnetic field canceling coil driver to supply current to the magnetic field canceling coil,
wherein the magnetic field canceling coil cancels a prepolarization magnetic field established on the wall of the magnetic shield room by a prepolarization coil disposed in the center of the magnetic shield room to minimize magnetic interference caused by the magnetic shield room,
wherein the magnetic field canceling coil driver is identical to a prepolarization coil driver to supply current to the prepolarization coil,
wherein the prepolarization coil is serially connected to the magnetic field canceling coil, and
wherein the magnetic shield room is made of a plurality of sheet materials having high magnetic permeability.

2. The apparatus according to claim 1, wherein the magnetic field canceling coil comprises:
a side coil disposed adjacent to the wall of the magnetic shield room parallel to a direction of the prepolarization magnetic field;
a top coil disposed at the side toward the prepolarization magnetic field among the wall of the magnetic shield room perpendicular to the direction of the prepolarization magnetic field; and
a bottom coil disposed at the side opposite to the prepolarization magnetic field among the wall of the magnetic shield room perpendicular to the direction of the prepolarization magnetic field.

3. The apparatus according to claim 2, wherein the side coil includes winding coils connected in series to surround the inside of the magnetic shield room including the prepolarization coil, and
wherein the turn number of the winding coils per unit length of the side coil is maximum in the center of the side coil and minimum at the both ends of the side coil.

4. The apparatus according to claim 2, wherein the top coil or the bottom coil includes winding coils of the different sizes that are connected in series on the same plane, and wherein the turn number of the winding coils decreases during increasing depending on a radial direction of the top coil or the bottom coil.

5. The apparatus according to claim 2, wherein the turn number of winding coils per unit length of the side coil is constant,
wherein the side coil is divided into a plurality of unit coils, and
wherein individual conductors constituting the unit coil are connected in parallel to adjust current density distribution according to a position of the side coil.

6. The apparatus according to claim 2, wherein the side coil comprise one or more winding coil bundles each including one or more winding coils connected in parallel,
wherein the winding coil bundles are connected in series, and
wherein current density of the side coil is maximum in the center of the side coil and minimum at both ends of the side coil.

7. The apparatus according to claim 1, wherein current flowing to the magnetic field canceling coil is synchronized with current flowing to the prepolarization coil, and
wherein current of a constant rate of the current flowing to the prepolarization coil flows to the magnetic field canceling coil.

8. The apparatus according to claim 1, wherein a portion of the magnetic field canceling coil is removable.

9. The apparatus according to claim 1, wherein the magnetic shield room further comprises a magnetic shield room door, and
wherein a portion of the magnetic field canceling coil adjacent to the magnetic shield room door is removable and the removable portion is fixedly coupled to the magnetic shield room door.

10. A magnetic resonance device comprising:
a magnetic shield room;
a magnetic field canceling coil disposed adjacent to an inner wall of the magnetic shield room to surround the entire inner wall or a portion of the inner wall of the magnetic shield room;
a prepolarization coil disposed in the center of the magnetic shield room; and
a magnetic field canceling coil driver to supply current to the magnetic field canceling coil,
wherein the magnetic field canceling coil cancels a prepolarization magnetic field established on the wall of the magnetic shield room by a prepolarization coil disposed in the center of the magnetic shield room and minimizes interference with magnetic resonance of a measurement target disposed inside the prepolarization coil,
wherein the magnetic field canceling coil driver is identical to a prepolarization coil driver to supply current to the prepolarization coil,
wherein the prepolarization coil is serially connected to the magnetic field canceling coil, and
wherein the magnetic shield room is made of a plurality of sheet materials having high magnetic permeability.

11. The magnetic resonance device according to claim 10, wherein the magnetic field canceling coil comprises:
a side coil disposed adjacent to the wall of the magnetic shield room parallel to a direction of the prepolarization magnetic field;
a top coil disposed at the side toward the prepolarization magnetic field among the wall of the magnetic shield room perpendicular to the direction of the prepolarization magnetic field; and
a bottom coil disposed at the side opposite to the prepolarization magnetic field among the wall of the magnetic shield room perpendicular to the direction of the prepolarization magnetic field.

12. A magnetic shield device comprising:
a magnetic shield room;
a magnetic field canceling coil disposed adjacent to an inner wall of the magnetic shield room to surround the entire inner space or a portion of inner space of the magnetic shield room; and
a magnetic field canceling coil driver to supply current to the magnetic field canceling coil,
wherein the magnetic field canceling coil cancels a prepolarization magnetic field established on the wall of the magnetic shield room by a prepolarization coil disposed in the center of the magnetic shield room to minimize magnetic interference caused by the magnetic shield room,
wherein the magnetic field canceling coil driver is identical to a prepolarization coil driver to supply current to the prepolarization coil,
wherein the prepolarization coil is serially connected to the magnetic field canceling coil, and
wherein the magnetic shield room is made of a plurality of sheet materials having high magnetic permeability.

13. The magnetic shield device according to claim 12, wherein the magnetic field canceling coil comprises:
a side coil disposed adjacent to the wall of the magnetic shield room parallel to a direction of the prepolarization magnetic field;
a top coil disposed at the side toward the prepolarization magnetic field among the wall of the magnetic shield room perpendicular to the direction of the prepolarization magnetic field; and
a bottom coil disposed at the side opposite to the prepolarization magnetic field among the wall of the magnetic shield room perpendicular to the direction of the prepolarization magnetic field.

* * * * *